US00PP16792P2

(12) United States Plant Patent
Austin

(10) Patent No.: US PP16,792 P2
(45) Date of Patent: Jul. 11, 2006

(54) SHRUB ROSE PLANT NAMED 'AUSBOSKY'

(50) Latin Name: *Rosa hybrida*
Varietal Denomination: AUSbosky

(75) Inventor: David C. H. Austin, Wolverhampton (GB)

(73) Assignee: David Austin Roses Ltd., Wolverhampton (GB)

( * ) Notice: Subject to any disclaimer, the term of this patent is extended or adjusted under 35 U.S.C. 154(b) by 41 days.

(21) Appl. No.: 11/034,406

(22) Filed: Jan. 11, 2005

(51) Int. Cl.
*A01H 5/00* (2006.01)

(52) U.S. Cl. ..... Plt./107

(58) Field of Classification Search ..... Plt./107, Plt./102, 149
See application file for complete search history.

*Primary Examiner*—Anne Marie Grunberg
*Assistant Examiner*—June Hwu
(74) *Attorney, Agent, or Firm*—Klarquist Sparkman LLP

(57) ABSTRACT

Shrub rose plant having pink, rosette-shaped blooms produced with exceptional continuity; dense growth; and warm and fruity fragrance.

1 Drawing Sheet

Genus and species: *Rosa hybrida.*
Variety denomination: 'AUSbosky'.

ORIGIN OF THE INVENTION

The present invention relates to a new and distinct variety of a shrub rose plant named 'AUSbosky' which was originated by me by crossing an unnamed, unpatented seedling ('AUSmas'×unnamed seedling) with an unnamed, unpatented seedling.

BACKGROUND OF THE INVENTION

The primary objective of this breeding was to produce a very free flowering and healthy variety rose plant, having pink blooms tinted with apricot at the center, and which forms a broad, dense shrub.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Pink, rosette-shaped blooms, produced with exceptional continuity.
2. Broad shrub with dense growth.
3. Warm fruity fragrance.

Asexual reproduction of this new variety by budding, as performed at Albrighton, England, shown that the foregoing and all other characteristics and distinctions come true to form and are established and transmitted through succeeding propagations.

Comparison with Parents

'AUSbosky' has pink blooms and more arching growth which differs from the white blooms of the seed parent. The blooms of the pollen parent are semi-double compared with the double blooms of 'AUSbosky' and the parent makes a narrower, less dense shrub.

Comparison with Similar Variety

'AUSled' (U.S. Plant Pat. No. 10,607) has paler peach-pink blooms than the pink blooms of 'AUSbosky' and less dense and less vigorous growth.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (2001), except where ordinary dictionary significance of color is indicated.

Parentage:
*Seed parent.*—Unnamed Seedling ('AUSmas'/Unnamed Seedling)(Unpatented).
*Pollen parent.*—Unnamed Seedling. (Unpatented).

FLOWER

Observations made from plants commencing at one year of age grown in a garden environment at Albrighton, England.

Blooming habit: Continuous. The number of blooms per plant during the growing season is profuse, but there are too many to count.

Bud:
*Size.*—About 3 cm long and 2.4 cm in diameter when the petals start to unfurl.
*Form.*—The bud form is long, pointed ovoid.
*Color.*—When sepals first divide, bud color is Red-Purple Group 58A. When half blown, the upper sides of the petals are Red Group 51B and Yellow-Orange Group 19B at their bases; and the lower sides of the petals are Red Group 37B and Yellow-Orange Group 15C at their bases.

*Sepals.*—Color: Upper surface: Yellow-Green Group 147D. Lower surface: Green Group 143B. Length: 2.6 cm. Width: 0.8–0.9 cm. Shape: Ovate. Surface texture: Upper surface: Rough. Lower surface: Pubescent. There are three normally appendaged sepals. There are two unappendaged sepals with canescent edges.

*Receptacle.*—Color: Yellow-Green Group 144B. Shape: Campanulate. Size: Medium, about 10 mm long×6 mm wide. Surface: Smooth.

*Peduncle.*—Length: Medium, averaging about 2.5 cm. Surface: Rough. Color: Yellow-Green Group 144A. Strength: Normal.

Bloom:

*Size.*—Medium. Average open diameter is about 7.5 cm.

*Borne.*—Several together in rounded clusters of four to fourteen blooms.

*Stems.*—Strength: Strong. Average length is about 29.5 cm with a diameter of 5 mm.

*Form.*—When first open: Cupped. Permanence: Flattens.

*Petalage.*—Number of petals under normal conditions: 51.

*Color.*—The upper sides of the petals are Red Group 55B. The reverse sides of the petals are Red Group 54C. The bases of the petals are yellow varying between Yellow Group 6A, Yellow Group 4C, and Yellow Group 9A. The major color on the upper side is Red Group 55B.

*Variegations.*—Margined.

*Discoloration.*—The general tonality at the end of the first day: Red Group 55B. At the end of the third day: Red-Purple Group 65C.

*Fragrance.*—Slight, fruity.

Petals:

*Texture.*—Smooth.

*Size.*—Width: 3.2 cm. Length: 4.3 cm.

*Surface.*—Smooth.

*Shape.*—Narrow elliptical. Margin: Weak undulation and slightly reflexing. Apex shape: Round, entire. Base shape: Cuneate. Form: Tips slightly recurved.

*Arrangement.*—Quartered.

*Petaloids.*—Number: 4. Color: Red-Purple Group 62A.

*Persistence.*—Petals drop off cleanly before drying.

*Lastingness.*—On the plant: Fair (about 3 days). As a cut flower: Short (about 3 days).

Reproductive parts:

*Stamens.*—Number: 77. Length: 5 mm. Anthers: Length: 1 mm. Color: Greyed-Orange Group N170A. Arrangement: Regular around styles. Filaments: Color: Greyed-Orange Group N167A. Length: 4 mm. Pollen: Color: Greyed-Orange Group N170A.

*Pistils.*—Number: 46. Length: 7 mm. Styles: Color: Green-Yellow Group 1C. Length: 6 mm. Stigmas: Color: Yellow-Green Group 154D. Length: 1 mm. Hips: None observed.

PLANT

*Form.*—Shrub.

*Growth.*—Vigorous, branching.

*Age at maturity.*—Two years.

*Mature plant.*—Height: 1.5 m. Width: 1.2 m.

*Rootstock.*—Dr. Huey in the United States. *Rosa dumetorum* 'Laxa' for the observed plants in the United Kingdom.

Foliage: Number of leaflets on normal mid-stem leaves: 5.

*Size.*—Large. About 12 cm long×9 cm wide.

*Quantity.*—Abundant. Average number leaves per flowering stem: 8.

*Color.*—New foliage: Upper side: Green Group 143A. Lower side: Green Group 139C. Old foliage: Upper side: Green Group 137A. Lower side: Green Group 139C.

Leaflets:

*Size.*—About 5 cm long×3.5 cm wide.

*Shape.*—Pointed oval.

*Base shape.*—Rounded.

*Apex shape.*—Acuminate.

*Texture.*—Leathery.

*Edge.*—Serrated.

*Serrations.*—Single and small.

*Petiole.*—Color: Green Group 143A.

*Petiole rachis.*—Color: Green Group 144B. Underside: Smooth with prickles.

*Auricle shape.*—Subulate.

*Stipules.*—Length: 2 cm, serrated.

*Disease resistance.*—Resistant to powdery and downy mildews, blackspot and rust under normal growing conditions.

*Pest resistance.*—Not tested.

*Vein color.*—Yellow-Green Group 144B.

*Venation pattern.*—Reticulate.

Wood:

*New wood.*—Color: Yellow-Green Group 144A. Bark: Smooth.

*Old wood.*—Color: Yellow-Green Group 144A. Bark: Rough.

Stems:

*Mature stem.*—Length: About 43 cm. Diameter: 9 mm. Internode distance: 7.5 cm.

Prickles:

*Quantity.*—On main canes from base: Ordinary, 23 per 30 cm per stem length. On laterals from main canes: Ordinary, 16 per 15 cm per stem length.

*Form.*—Hooked downward.

*Length.*—7 mm.

*Color when young.*—Red Group 36C.

*Color when mature.*—Greyed-Orange Group 165B.

Small prickles:

*Quantity.*—On main stalks: Ordinary. Number per stem length: 23 per 35 cm of stem. On laterals: Ordinary. Number per stem length: 17 per 35 cm of stem.

*Color.*—When young: Orange Group 27B. When mature: Greyed-Orange Group 164B.

Winter hardiness: Not tested.

I claim:

1. A new and distinct variety of rose plant of the shrub class, substantially as herein shown and described, characterized particularly by its pink, rosette-shaped blooms produced with exceptional continuity; dense growth; and warm and fruity fragrance.

* * * * *

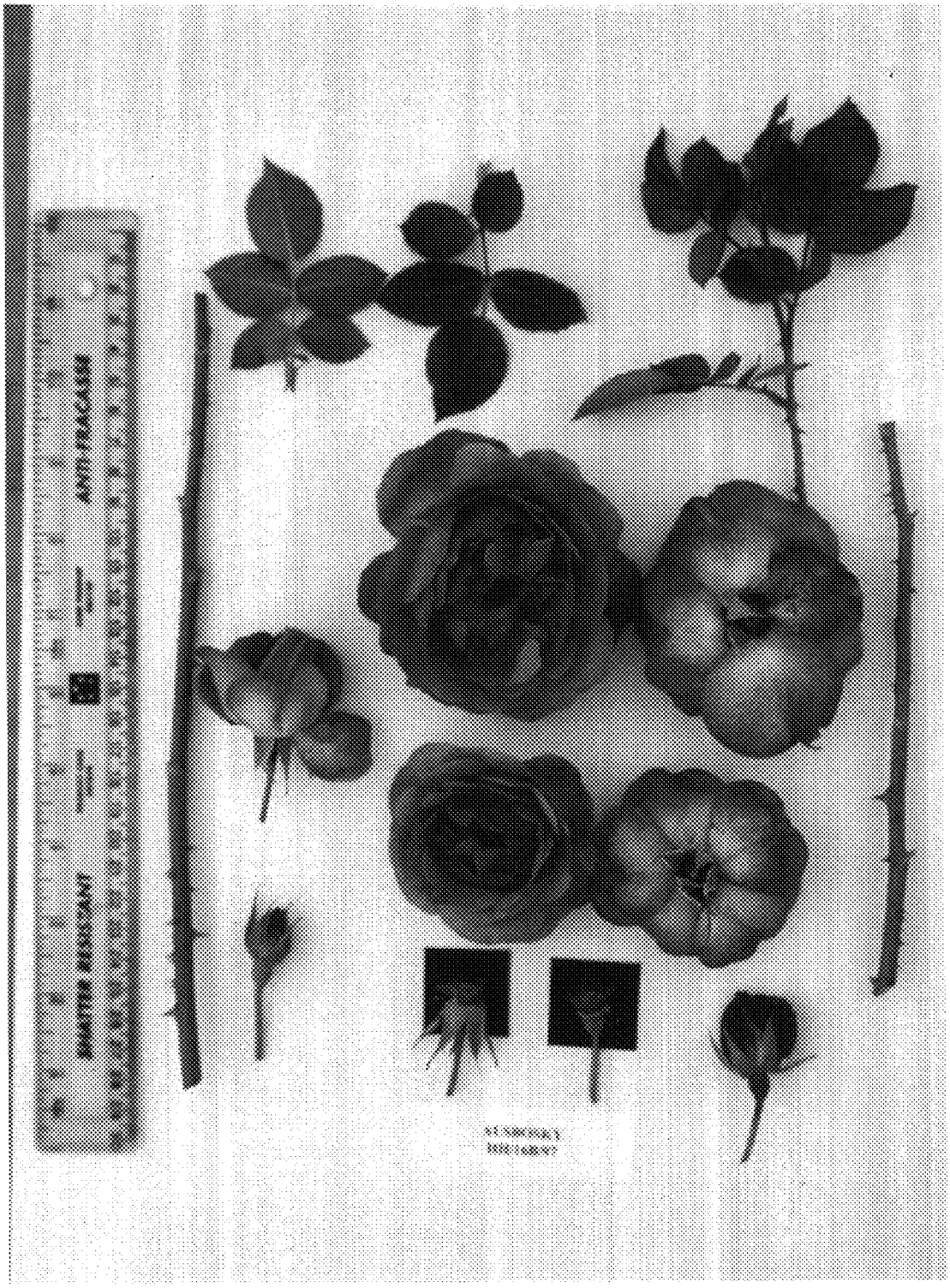
SHATTER RESISTANT
ANTI-FRACASS